United States Patent [19]

Wallace

[11] 4,307,903
[45] Dec. 29, 1981

[54] ANTIDISCONNECT HARNESS FOR MEDICAL CONNECTIONS

[75] Inventor: Dean R. Wallace, Ft. Myers, Fla.

[73] Assignee: Airco, Inc., Montvale, N.J.

[21] Appl. No.: 4,962

[22] Filed: Jan. 19, 1979

[51] Int. Cl.³ .............................................. F16L 13/04
[52] U.S. Cl. ................................ 285/114; 128/207.14;
285/334.5; 285/397; 285/423; 285/255; 24/16 PB
[58] Field of Search .................. 285/8, 114, 242, 255,
285/334.5, 397, 423; 128/DIG. 26, 351, 208;
24/201 HE, 16 PB; 228/207.14

[56] References Cited

U.S. PATENT DOCUMENTS 3,695,632  10/1972  Kruse .................................. 285/255

Primary Examiner—Dave W. Arola
Attorney, Agent, or Firm—Roger M. Rathbun; Larry R. Cassett

[57] ABSTRACT

An antidisconnect device is provided to prevent the inadvertent separation of medical fittings or connectors normally provided on the external end of a patient connected medical device such as an endotracheal or tracheostomy tube. The antidisconnect device basically comprises an annular ring having an internal diameter adapted to slip in close engagement over the normal outside diameter of the medical tubing. When assembled, the medical tubing is forced onto the tapered endotracheal tube connector thus distorting and enlarging the outside diameter of the medical tubing to a diameter larger than the internal diameter of the antidisconnect device. The antidisconnect device can then be moved toward the endotracheal tube tapered connector and can be forcefully held in position against the expanded diameter of the medical tubing. A strap extends from the annular ring to encircle any fitting or connector extending from the medical tubing to the patient and the distal end of the strap is affixed to the annular ring. Thus, any connector or fitting is encircled by the strap and disengagement by loosening of the tapered connections is prevented.

4 Claims, 3 Drawing Figures

ANTIDISCONNECT HARNESS FOR MEDICAL CONNECTIONS

BACKGROUND OF THE INVENTION

In present use today are a variety of disposable, as well as non-disposable tubings used to deliver a gas to a patient for medical purposes. The gas may be supplied by means of anesthesia gas machines, ventilators or respirators through such tubing and the gas ultimately introduced to the patient through a tracheostomy tube or endotracheal tube for introduction and removal thereof from the patient's lungs.

The tubing carrying such gas is readily connectible to other devices, such as the gas machine or endotracheal tubing through the use of tapered connections, on which the relatively resilient tubing is forced. In most instances, there may be two or even more of such tapered, forced connections between the tubing and the actual device administering gas to the patient. As such, therefore, the tightness and integrity of such couplings depend significantly upon the amount of force used to join such connections and fittings which are generally relatively rigid.

This means of connection is, of course, readily made and is readily disconnected, however, there is much concern today about the problem of accidental or inadvertent disconnection of such couplings using tapered fittings.

The matter is, of course, of particular criticality in those instances where life support gases are being administered to a patient otherwise unable to self-breathe. In such instances, a disconnection can cause death or permanent brain damage in the relatively short time prior to discovery by attending personnel. Even in those instance where personnnel are continually monitoring the patient and an inadvertent disconnection readily reconnected, there is a need to eliminate the risk that may be occasioned by the disconnection.

There have been proposals, systems to prevent such disconnection of tubing from tapered connections by providing slots, rings or some extensions on the mating external surfaces of tubing and connection, such that elastic bands or other tying means can be used to secure the parts in their connected relationship. One difficulty of projections and the like, however, is that such projection must be kept free of sharp edges or points that could injure the patient, then such must be kept smooth and restricted to a maximum amount of extension from the normal surface of the component. One proposal presently under consideration is to keep any such projections to a maximum of 4 mm. from the component surface.

SUMMARY OF THE INVENTION

The present invention fills the need for a means to prevent the inadvertent or accidental disconnection of fittings and connectors by providing an antidisconnect device that is adapted as an addition to be used with existing tubing and fittings and thus avoids the necessity of changing present tubing or fittings.

The antidisconnect device comprises an annular ring that is of predetermined dimensions, such that its internal diameter slides snugly over the outside diameter of the particular tubing in its normal form. As that tubing is forced upon a tapered connector, the tubing diameter (both internal and external) of the tubing is increased in accordance with the particular taper of the connector. The diameter of the tubing conforms to the tapered connector and a neck is formed on the end of the tubing as it is forced onto such connector.

The antidisconnect device can thus be held in position since the dimension of its inside diameter prevents its further movement in the direction that the tubing outside diameter is increasing.

Since the external diameter of the tubing at the enlarged neck portion is larger than the internal diameter of the antidisconnect device, that device will be stopped in a force fit with the enlarged neck. A strap is provided which is adapted to encircle connections and fittings and both ends of the strap are affixed to the annular ring, thus, the connections and fittings are held together by the strap and cannot easily be inadvertently disconnected.

Thus, an antidisconnect device is produced that adapts to present convenational tubing and forcefully holds tapered connections typical of medical fittings and connectors, yet no extensive projections are required that could hamper or impede the normal operations being carried on with that patient.

The overall invention is illustrated in the accompanying drawings showing a preferred embodiment thereof.

DESCRIPTION OF THE PREFERRED EMBODIMENT

Figure 1:
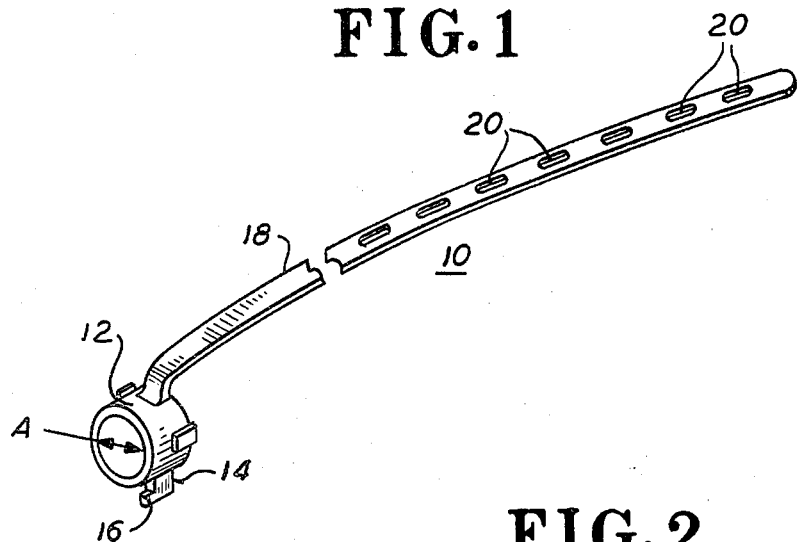
FIG. 1 is an isometric view of the antidisconnect device which is the subject matter of the invention hereof.

In FIG. 1 there is shown an antidisconnect device 10 constructed in accordance with the present invention. The device 10 comprises an annular ring 12 which is preferably fabricated or molded from a semi-flexible thermoplastic material, such as polyvinylchloride. The annular ring 12 has an inside diameter A of a predetermined dimension for reasons that will later become apparent. A projection 14 is also integrally molded with ring 12 and projects outwardly therefrom and includes an extension 16 that points generally coaxially with respect to the annular ring 12. A strap 18, also preferably integrally molded with ring 12, extends from the annular ring on its periphery approximately 180° from the projection 14.

Along the length of the strap 18, there are formed oval shaped holes 20. As shown, a plurality of holes 20 are employed and again, are formed during the molding process such that the entire antidisconnect device 10 may be molded as a unitary piece.

Figure 2:
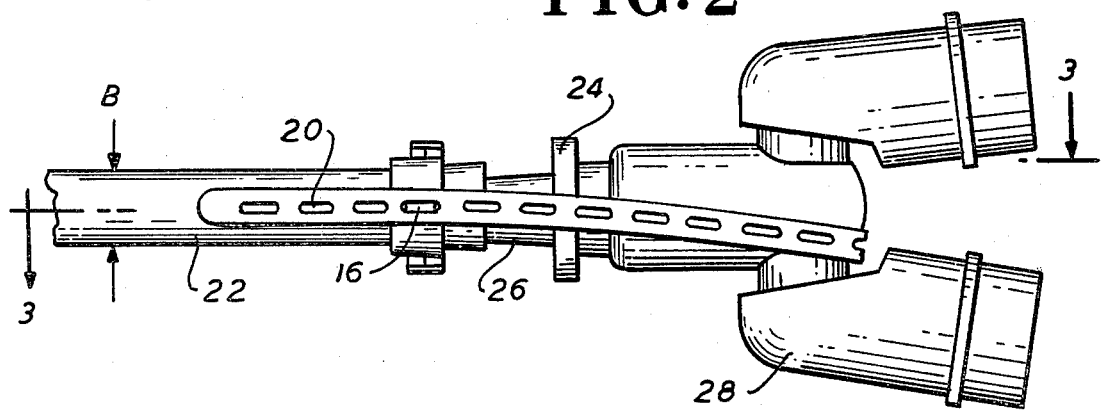
FIG. 2 is a plan view of the antidisconnect device of FIG. 1 in position on a medical tubing and holding together tapered connections of a connector and a Y-piece.
Figure 3:
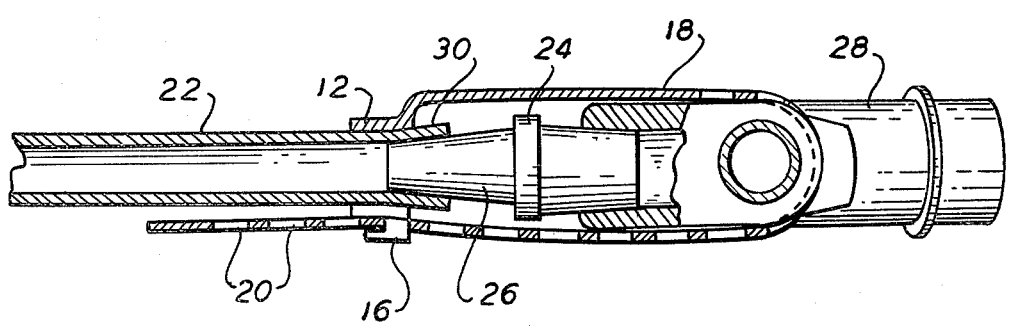
FIG. 3 is a side view, partly in cross-section of the connection of FIG. 2.

Turning now to FIGS. 2 and 3, the antidisconnect device 10 is illustrated in position in use holding the end of a medical tubing 22 on a tapered connector 24. The tubing 22 is typically of a relatively resilient material such as polyvinylchloride. In the description that follows of the subject invention, it may be easily seen that the tubing 22 may itself be the proximal end of an endotracheal tube or tracheostomy tube since the same are normally provided in certain standard sizes for connection with standard connectors for medical uses.

In the illustration, therefore, a tubing 22 will be referred to and which is normally joined to a connector 24 having a tapered end 26 of connector 24 and the tubing 22 if of sufficient resilience such as to distort to conform to the taper as it is forced thereon, thereby creating a gas-tight force fit with connector 24.

The typical connector 24 is relatively rigid to receive tubing 22 and has its other end also formed as a tapered fitting. In a usual patient circuit, the other end is connected by force fit to other parts of the circuit supplying gas to the patient, such as a Y-piece 28 and which is also relatively rigid. The tapered connection between connector 24 and Y-piece 28 is susceptible of accidental or inadvertent uncoupling since the integrity of the connector relies upon a force fit between two relatively rigid, tapered surfaces.

The use of the antidisconnect device 10 will now be explained. The tubing 22, as described, is normally joined to the connector 24 by being forced upon the tapered end 26. The annular ring 12 is prepositioned upon the tubing 22 and the inside diameter A is of such a dimension such as to allow a relatively tight, sliding fit along the normal outside diameter B of the tubing 22. As the tubing 22 is fit upon the tapered end 26 of connector 24, however, the diameter B is distorted to conform to the taper and is expanded to a larger diameter at its proximal end, thus forming a shoulder 30 having an increased diameter that is larger than the inside diameter A of the annular ring 12.

The device 10 can thus be slipped along the tubing 22 in the direction toward connector 24 and forced against the shoulder 30 where it encounters the shoulder 30 and is held thereagainst by its own flexibility, conforming slightly to the increased diameter of shoulder 30. The strap 18 can now be encircled around some portion of the circuit fixed relative to the fitting 24 and its end secured to the antidisconnect device 10 by inserting the projection 14 through one of the appropriate holes 20, thus retaining the antidisconnect device 10 in its position fitted snugly against shoulder 30.

As shown, the strap 18 has one end molded integrally to the annular ring 12 and is of sufficient length, depending upon the fitting or other devices to be encircled, to encircle those connectors, fittings or the like, and the free end reach back to the annular ring 12 where a means is provided to secure that free end. As can be readily seen, the strap 18 may include a variety of alternate means to secure its free end to the annular ring 12, or may even be entirely free and have a means to secure both of its then free ends to the annular ring 12.

As may now be seen, the operation of the antidisconnect device 10 is activated by a force tending to separate connector 24 from Y-piece 28. The external pulling force is effectively transferred to the strap 18 as a tensile load which in turn transfers that tensile load to the annular ring 12 through the end of strap 18 connected to annular ring 12. The load thereby transferred to the annular ring 12 causes that ring 12 to more firmly abut against and hold the shoulder 30 since the outside diameter of that shoulder 30 is larger than the inside diameter A of the antidisconnect device 10. The strap 18 is thus effectively and firmly held in the position encircling and thus holding together those tapered connections where separation is most likely, in this instance, the tapered, semi-rigid connector between connector 24 and Y-piece 28.

As an example of the diameter relationships needed to create an operative antidisconnect device, an 8 mm endotracheal tube is forced onto a typical tapered fitting, the outside diameter of the tube expands approximately 0.020 inches. An operative slip fit between such endotracheal tube and the inside diameter of an antidisconnect device can be effected through an inside diameter of the order of about 0.436–0.440 inches. As is obvious, a separate antidisconnect device of predetermined diameters is required for each standard endotracheal tube or other medical tubing to be attached to a tapered fitting.

It will be understood that the scope of the method and product of this invention is not limited to the particular steps or materials disclosed herein, by way of example, but only by the scope of the appended claims.

I claim:

1. An antidisconnect device to prevent the disconnection between various tapered fitting connectors adapted to be forced into a medical tubing creating a circumferentially continuous end of increased diameter thereof and a device administering gas to a patient through the tubing, said device comprising:

a semi-flexible annular ring of predetermined inside diameter, said inside diameter being approximately the same dimension as the outside diameter of said tubing, such that said annular ring slides tightly over said tubing and which inside diameter is smaller than the increased diameter end of said tubing, said annular ring being sufficiently flexible to flex and distort as it is slid against the increased diameter end of said tubing to form a gas tight fit between said tubing and the tapered fitting connector;

strap means having one end integrally molded to said ring and being of predetermined length to encircle the connectors joined to said tubing; and securing means to secure the other end of said strap means to said annular ring, said securing means adapted to secure said strap at a plurality of positions along said strap wherein said strap can tightly encircle said connectors and hold said connectors from moving away from said annular ring, thus preventing disconnection thereof.

2. An antidisconnect device as defined in claim 1 wherein the free end of said strap has a plurality of holes or projections adapted to be affixed at one of a plurality of positions to a corresponding projection or hole on said annular ring.

3. An antidisconnect device as defined in claim 2 wherein the free end of said strap means includes a plurality of spaced holes in said strap, said holes adapted to be selectively affixed to a projection integrally molded on said annular ring.

4. A method of preventing the disconnection of tapered fitting connectors joined to a medical tubing comprising the steps of:

fitting a semi-flexible annular ring having an inside diameter of predetermined dimension such that said ring surrounds and tightly is movable along the tubing;

forcing one end of the tubing upon a tapered male connector such that the tubing is distorted and its outside diameter is increased about said tapered connector to form a circumferentially continuous end of a diameter larger than the inside diameter of the annular ring;

sliding said annular ring against said increased diameter end such that said annular ring flexes and distorts to create a gas tight fit between said tubing and said tapered connector; and encircling a strap having one end integrally molded to annular ring and the other end adjustably connectible to said annular ring about the tapered connector such that said strap holds said connector to the tubing.

* * * * *